United States Patent [19]

Cooper

[11] Patent Number: 4,518,531

[45] Date of Patent: May 21, 1985

[54] ALLYLIC CHLORINATION PROCESS AND COMPOUNDS PREPARED THEREBY

[75] Inventor: Robin D. G. Cooper, Indianapolis, Ind.

[73] Assignee: Eli Lilly and Company, Indianapolis, Ind.

[21] Appl. No.: 550,854

[22] Filed: Nov. 14, 1983

Related U.S. Application Data

[60] Division of Ser. No. 130,888, Mar. 17, 1980, , which is a continuation-in-part of Ser. No. 34,825, Apr. 30, 1970, abandoned.

[51] Int. Cl.$^3$ ............... C07D 205/08; C07D 513/14; C07B 9/00
[52] U.S. Cl. .................................................. 260/245.4
[58] Field of Search ....................................... 260/245.4

[56] References Cited

U.S. PATENT DOCUMENTS 4,079,181  3/1978  Tsuji et al. ................... 260/245.4

OTHER PUBLICATIONS

Uveo et al., *Heterocycles* 10, 99–104, (1978).

Primary Examiner—Mark L. Berch
Attorney, Agent, or Firm—Joseph A. Jones; Arthur R. Whale

[57] ABSTRACT

This invention provides a novel allylic chlorination process for inserting a chlorine atom on the saturated methyl group of a 3-methyl-2-but-3-enoate group on the ring nitrogen atom of a 2-azetidinone or thiazolinoazetidinone. The chloro-substituted compounds prepared thereby are novel intermediates used in preparation of cephalosporins.

10 Claims, No Drawings

ALLYLIC CHLORINATION PROCESS AND COMPOUNDS PREPARED THEREBY

CROSS-REFERENCE

This application is a division, of application Ser. No. 130,888, filed Mar. 17, 1980 which is a continuation-in-part of Ser. No. 34,825, filed Apr. 20, 1979 and now abandoned.

BACKGROUND OF THE INVENTION

1. Field of the Invention

This invention concerns the synthesis of antibiotic compounds of the cephalosporin series.

Azetidinones and thiazolinoazetidinones are now well known as intermediates for preparing cephalosporins. A variety of synthetic routes have been published. In general, all of them proceed by first opening the 5-membered ring of a penicillin to form a thiazolinoazetidinone. The 5-membered ring of these compounds may be opened to form the corresponding azetidinone. Modifications are made to the group on the nitrogen atom of the azetidinone ring (whether fused or not) and the resulting compound is re-cyclized to form the desired cephalosporin. The following publications are representative of those which describe such processes: Belgian Pat. Nos. 864,321, 832,174, 862,793, 863,700, 863,998, U.S. Pat. Nos. 4,079,181, 4,013,653, 4,077,970, British Pat. Nos. 1,472,863 through 1,472,870, and U.S. Pat. No. 4,018,776.

2. Prior Art

Some previous publications show or suggest halogenation of the butenoate group on an azetidinone or thiazolinoazetidinone. Particular attention is given to Belgian Pat. No. 862,793, where such a halogenation is performed on a 3-methyl-2-but-3-enoate group. This patent, of May 2, 1978, however, teaches generally that bromine, chlorine or iodine atoms may be inserted with the use of free radical initiators. N-Bromosuccinimide in the presence of azobisisobutyronitrile is emphasized in the patent, although sulfuryl chloride and molecular chlorine are also used. The patent shows that the oxazolinoazetidinones which are its starting compounds frequently have the oxazoline ring opened by the halogenation step, and that the methylbutenoate group is isomerized so that a mixture of products is obtained.

Belgian Pat. No. 864,321 shows the chlorination of a similar group on an oxazolinoazetidinone by molecular chlorine and strong light. However, a second chlorine atom is also added on the 3-carbon atom.

U.S. Pat. No. 4,077,970 and British Pat. Nos. 1,472,863 through 1,472,870 suggest the halogenation of a methylbutenoate group on a thiazolinoazetidinone. However, the halogenations which these patents show cause the isomerization of the 3-butenoate group to a 2-butenoate group.

SUMMARY OF THE INVENTION

The invention described here provides an allylic chlorination process which can cleanly insert a chlorine atom on the saturated methyl group of a 3-methyl-2-but-3-enoate group on the ring nitrogen atom of a 2-azetidinone ring. The process may be used on azetidinones as such, or on azetidinones which are fused with a thiazoline group. The chloro-substituted compounds which are prepared by the use of this process are novel intermediates which are useful in preparing antibiotic compounds of the cephalosporin series. The allylic chlorination of this invention proceeds in economical yields at moderate temperatures. The chlorinating agents are molecular chlorine or t-butyl hypochlorite in any of a range of organic solvents, of which esters are preferred.

The particularly advantageous feature of the process of this invention is its ability to chlorinate the 3-methyl-2-but-3-enoate group without undue isomerization of the group to the corresponding 3-methyl-2-but-2-enoate group, or chlorinating the compound at any other location.

Accordingly, the invention also provides novel compounds which were not accessible prior to this invention. The novel compounds are of the formula

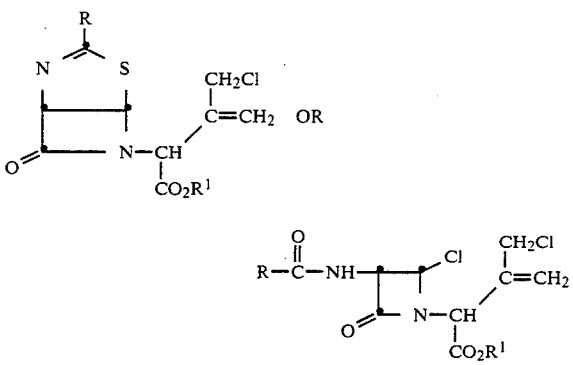

wherein
R is hydrogen,
methoxy,
$C_1$–$C_2$ alkoxycarbonyl,
$C_1$–$C_8$ alkyl,
$C_1$–$C_8$ alkyl monosubstituted with protected hydroxy, $C_1$–$C_3$ alkoxy or cyano,
$C_2$–$C_8$ alkenyl,
$C_2$–$C_8$ alkenyl monosubstituted with protected hydroxy, $C_1$–$C_3$ alkoxy or cyano,
$C_3$–$C_8$ cycloalkyl,
$C_3$–$C_8$ cycloalkyl substituted with protected hydroxy, $C_1$–$C_3$ alkoxy or cyano,

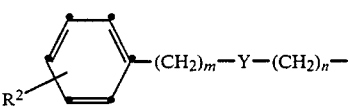

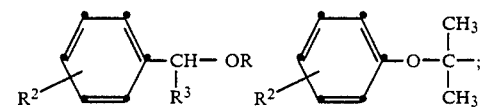

$R^2$ is hydrogen, protected hydroxy, chloro, bromo, $C_1$–$C_3$ alkyl, $C_1$–$C_3$ alkoxy, nitro or cyano;
Y is oxygen or a carbon-carbon bond;
$R^3$ is protected hydroxy, $C_1$–$C_4$ alkyl, or protected amino;
m is 0–2;
n is 0–2;
$R^1$ is a carboxylic acid protecting group; provided 1- and 5-position C–H bonds in the thiazolinoazetidinone are in the α-position.

The novel compounds above are made by the novel process comprising reacting a compound of the

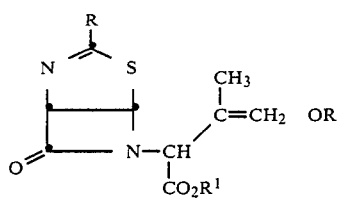

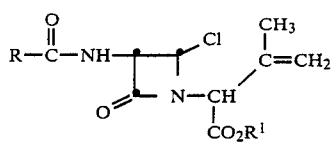

wherein the 1- and 5-positions are in the configuration described above, with molecular chlorine or t-butyl hypochlorite in the presence of a $C_1$–$C_3$ carboxylic acid; provided that, when the starting compound is a thiazolinoazetidinone, and molecular chlorine is used, a hydrochloric acid scavenger is also present.

DESCRIPTION OF THE PREFERRED EMBODIMENTS

The ring systems which form the nuclei of the compounds discussed herein will be named according to *Chemical Abstracts* nomenclature. The ring systems are numbered as follows.

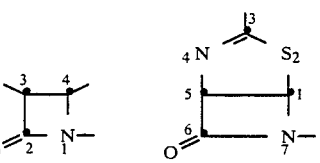

Thus, the fused-ring nucleus of a compound of this invention would be called a 2-thia-4,7-diazabicyclo-[3.2.0]hept-3-en-6-one.

It must be noted that the thiazolinoazetidinones of this invention, and their respective starting compounds, have the $C_1$-H and $C_5$-H bonds in the α configuration. The thiazolinoazetidinone ring system is shown graphically as follows.

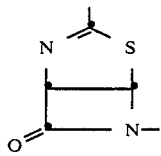

The various terms used in the descriptions above are used as they normally are in organic chemistry. For example, the term $C_1$–$C_2$ alkoxycarbonyl includes methoxycarbonyl and ethoxycarbonyl.

The terms $C_1$–$C_8$ alkyl, substituted $C_1$–$C_8$ alkyl, $C_2$–$C_8$ alkenyl, substituted $C_2$–$C_8$ alkenyl, $C_1$–$C_3$ alkoxy, $C_1$–$C_3$ alkyl, $C_1$–$C_4$ alkyl, $C_4$–$C_6$ t-alkyl and $C_5$–$C_8$ t-alkenyl include such groups as methyl, ethyl, isopropyl, hexyl, 2-ethylbutyl, neopentyl, octyl, 3-methylheptyl, 4-octyl, t-butyl, 3-propyl-3pentyl, formyloxymethyl, 3-benzyloxypentyl, 8-t-butoxyoctyl, 2-methoxyethyl, 6-propoxyhexyl, 4-ethoxyoctyl, 3-cyanopropyl, cyanomethyl, 7-cyanoheptyl, vinyl, allyl, 5-hexenyl, 1,1-dimethylallyl, 4-heptenyl, 2-octenyl, 1-chloroacetoxyallyl, 5-formyloxy-3-pentenyl, 8-benzyloxy-4-octenyl, 2-methoxyvinyl, 3-propoxyallyl, 8-ethoxy-2,6-octadienyl, 2-cyanoallyl, 3-cyano-2-pentenyl, 8-cyano-4-octenyl, ethyl, methoxy, isopropoxy, 2-butyl, 1,1-dimethylbutyl, 1,1-dimethyl-2-propenyl, 1,1-dimethyl-3-hexenyl, and 1,1-diethyl-2-butenyl.

The terms $C_3$–$C_8$ cycloalkyl and substituted $C_3$–$C_8$ cycloalkyl include such groups as cyclopropyl, cyclopentyl, cycloheptyl, cyclooctyl, 2-methoxymethoxycyclobutyl, 3-formyloxycyclohexyl, 2-benzyloxycyclooctyl, 2-ethoxycyclopropyl, 2-methoxycyclohexyl, 4-isopropoxycyclooctyl, 2-cyanocyclohexyl, 3-cyanocyclooctyl and 2-cyanocyclopropyl.

The term protected amino refers to an amino group substituted with one of the commonly employed aminoprotecting groups such as t-butoxycarbonyl, benzyloxycarbonyl, 4-methoxybenzyloxycarbonyl, 4-nitrobenzyloxycarbonyl, 2,2,2-trichloroethoxycarbonyl and 1-carbomethoxy-2-propenyl. Other accepted aminoprotecting groups such as are described by J. W. Barton in *Protective Groups in Organic Chemistry*, J. F. W. McOmie, Editor, Plenum Press, New York, 1973, chapter 2 will be recognized by organic chemists as suitable for the purpose.

The term, a carboxylic acid protecting group, refers to any group which is conventionally used to block or protect the carboxylic acid functionality of a cephalosporin or penicillin while reactions involving other functional sites are carried out. Such carboxylic acid protecting groups are noted for their ease of cleavage and for their ability to protect the acid from unwanted reactions. Such groups are thoroughly described by E. Haslam in *Protective Groups in Organic Chemistry*, Chapter 5. Any such group may be used, of course. The preferred groups, however, are $C_1$–$C_4$ alkyl, $C_4$–$C_6$ t-alkyl, $C_5$–$C_8$ t-alkenyl, benzyl, methoxybenzyl, nitrobenzyl, diphenylmethyl, phthalimidomethyl, succinimidomethyl or trichloroethyl.

Similarly, the term protected hydroxy refers to groups formed with a hydroxy group such as formyloxy, 2-chloroacetoxy, benzyloxy, diphenylmethoxy, triphenylmethoxy, 4-nitrobenzyloxy, trimethylsilyloxy, phenoxycarbonyloxy, t-butoxy, methoxymethoxy and tetrahydropyranyloxy. Other accepted hydroxy-protecting groups, such as those described by C. B. Reese in chapter 3 of *Protective Groups in Organic Chemistry* will be understood to be included in the term protected hydroxy.

It is believed that the above formulae and discussion are adequate to define completely the novel compounds provided by this invention. However, in order to assure that anyone of skill in organic chemistry can obtain the compounds, the following group of exemplary compounds are mentioned methyl 2-(4-chloro-3-formamido-2-oxo-1-azetidinyl)-3-chloromethyl-3-butenoate ethyl 2-(4-chloro-3-methoxyformamido2-oxo-1-azetidinyl)-3-chloromethyl-3-butenoate isopropyl 2-(4-chloro-3-methoxyoxalylamino2-oxo-1-azetidinyl)-3-chloromethyl-3-butenoate butyl 2-(4-chloro-3-acetamido-2-oxo-1-azetidinyl)-3-chloromethyl-3-butenoate t-butyl 2-(4-chloro-3-propionamido-2-oxo-1-azetidinyl)-3-chloromethyl-3-butenoate 1,1-dimethylpropyl 2-[4-chloro-3-(2-methylpropionamido)-2-oxo-1-azetidinyl]-3-chloromethyl-3-butenoate 1,1-dimethylallyl 2-[4-chloro-3-(2-methylbutyramido)-2-oxo-1-azetidinyl]-3-chloromethyl-3-butenoate 1,1-diethyl-2-butenyl 2-[4-chloro-3(2-ethylvaleramido)-2-oxo-1-azetidinyl]-3-chloromethyl-3-butenoate benzyl 2-(4-chloro-3-nonanamido-2-oxo-1-azetidinyl)-3-chloromethyl-3-butenoate 3-methoxybenzyl 2-[4-chloro-3-(3-formyloxypropionamido)-2-oxo-1-azetidinyl]-3-chloromethyl-3-butenoate 4-nitrobenzyl 2-[4-chloro-3-(4-benzyloxyhexanamido)-2-oxo-1-azetidinyl]-3-chloromethyl-3-butenoate 3-nitrobenzyl 2-[4-chloro-3-(9-chloroacetoxynonanamido)-2-oxo-1-azetidinyl]-3-chloromethyl3-butenoate diphenylmethyl 2-(4-chloro-3-methoxyacetamido-2-oxo-1-azetidinyl)-3-chloromethyl-3-butenoate phthalimidomethyl 2-[4-chloro-3-(6-propoxyhexanamido)-2-oxo-1-azetidinyl]-3-chloromethyl-3-butenoate succinimidomethyl 2-[4-chloro-3-(4-ethoxynonanamido)-2-oxo-1-azetidinyl]-3-chloromethyl-3-butenoate 2,2,2-trichloroethyl 2-[4-chloro-3-(2-cyanopropionamido)-2-oxo-1-azetidinyl]-3-chloromethyl-3-butenoate t-butyl 2-[4-chloro-3-(5-cyanovaleramido)-oxo-1-azetidinyl]-3-chloromethyl-3-butenoate 4-nitrobenzyl 2-[4-chloro-3-(8-cyanooctanamido)-2-oxo-1-azetidinyl]-3-chloromethyl-3-butenoate benzyl 2-[4-chloro-3-(3-butenamido)-2-oxo-1-azetidinyl]-3-chloromethyl-3-butenoate methyl 2-[4-chloro-3-(5-hexenamido)-2-oxo-1-azetidinyl]-3-chloromethyl-3-butenoate 3-nitrobenzyl 2-[4-chloro-3-(8-nonenamido)-oxo-1-azetidinyl]-3-chloromethyl-3-butenoate ethyl 2-[4-chloro-3-(3-methoxymethoxy-3-butenamido)-2-oxo-1-azetidinyl]-3-chloromethyl-3-butenoate t-butyl 2-[4-chloro-3-(5-formyloxy-3-pentenamido)-2-oxo-1-azetidinyl]-3-chloromethyl-3-butenoate 4-nitrobenzyl 2-[4-chloro-3-(8-trimethylsilyloxy-3,6-nonadienamido)-2-oxo-1-azetidinyl]-3-chloromethyl-3-butenoate isopropyl 2-[4-chloro-3-(3-methoxy-2-propenamido)-2-oxo-1-azetidinyl]-3-chloromethyl-3butenoate benzyl 2-[4-chloro-3-(3-ethoxy-3-pentenamido)-2-oxo-1-azetidinyl]-3-chloromethyl-3-butenoate 3-methoxybenzyl 2-[4-chloro-3-(9-propoxy-3-nonenamido)-2-oxo-1-azetidinyl]-3-chloromethyl-3butenoate methyl 2-[4-chloro-3-(3-cyano-3-butenamido)-2-oxo-1-azetidinyl]-3-chloromethyl-3-butenoate trimethylsilyl 2-[4-chloro-3-(6-cyano-2-hexenamido)-2-oxo-1-azetidinyl]-3-chloromethyl-3-butenoate 4-methoxybenzyl 2-[4-chloro-3-(5-cyano-2-nonenamido)-2-oxo-1-azetidinyl]-3-chloromethyl-3-butenoate succinimidomethyl 2-(4-chloro-3-cyclopropylformamido-2-oxo-1-azetidinyl)-3-chloromethyl-3-butenoate diphenylmethyl 2-(4-chloro-3-cyclopentylformamido-2-oxo-1-azetidinyl)-3-chloromethyl-3-butenoate 2,2,2-trichloroethyl 2-(4-chloro-3-cyclohexylformamido-2-oxo-1-azetidinyl)-3-chloromethyl-3-butenoate t-butyl 2-(4-chloro-3-cyclooctylformamido-2-oxo-1-azetidinyl)-3-chloromethyl-3-butenoate benzyl 2-[4-chloro-3-(2-benzyloxycyclobutylformamido)-2-oxo-1-azetidinyl]-3-chloromethyl-3-butenoate 4-nitrobenzyl 2-[4-chloro-3-(4-formyloxycyclohexylformamido)-2-oxo-1-azetidinyl]-3-chloromethyl-3-butenoate diphenylmethyl 2-[4-chloro-3-(3-diphenylmethoxycyclooctylformamido)-2-oxo-1-azetidinyl)-3-chloromethyl-3-butenoate 3-nitrobenzyl 2-[4-chloro-3-(2-methoxycyclooctylformamido)-2-oxo-1-azetidinyl]-3-chloromethyl-3-butenoate diphenylmethyl 2-[4-chloro-3-(3-ethoxycycloheptylformamido)-2-oxo-1-azetidinyl]-3-chloromethyl-3-butenoate 2,2,2-trichloroethyl 2-[4-chloro-3-(3-propoxycyclopentylformamido)-2-oxo-1-azetidinyl]3-chloromethyl-3-butenoate succinimidomethyl 2-[4-chloro-3-(2-methoxycyclopropylformamido)-2-oxo-1-azetidinyl]-3-chloromethyl-3-butenoate diphenylmethyl 2-[4-chloro-3-(2-cyanocyclobutylformamido)-2-oxo-1-azetidinyl]-3-chloromethyl-3-butenoate triphenylmethyl 2-[4-chloro-3-(3-cyanocyclohexylformamido)-2-oxo-1-azetidinyl]-3-chloromethyl-3-butenoate benzyl 2-(4-chloro-3-(4-cyanocyclooctylformamido)-2-oxo-1-azetidinyl)-3-chloromethyl-3-butenoate methyl 2-(4-chloro-3-phenoxyacetamido-2-oxo-1-azetidinyl)-3-chloromethyl-3-butenoate 4-nitrobenzyl 2-(4-chloro-3-phenylacetamido-2-oxo-1-azetidinyl)-3-chloromethyl-3-butenoate benzyl 2-[4-chloro-3-(4-formyloxybenzyloxyacetamido)-2-oxo-1-azetidinyl]-3-chloromethyl-3-butenoate 2,2,2-trichloroethyl 2-[4-chloro-3-[3[3-chloroacetoxyphenyl)propionamido]-2-oxo-1azetidinyl]-3-chloromethyl-3-butenoate diphenylmethyl 2-[4-chloro-3-[2-(2-benzyloxyphenyl)ethoxyacetamido]-2-oxo-1-azetidinyl]-3-chloromethyl-3-butenoate benzyl 2-[4-chloro-3-[3-[2-(4-diphenylmethoxyphenyl)ethoxy]propionamido]-2-oxo-1-azetidinyl]3-chloromethyl-3-butenoate triphenylmethyl 2-[4-chloro-3-(3-triphenylmethoxybenzyloxyacetamido)-2-oxo-1-azetidinyl]-3-chloromethyl-3-butenoate 4-methoxybenzyl 2-[4-chloro-3-[2-trimethylsilyloxy-2-[4-(4-nitrobenzyloxy)phenyl]acetamido]-2-oxo-1-azetidinyl]-3-chloromethyl-3-butenoate methyl 2-[4-chloro-3-[2-(t-butoxy)-2(2-phenoxycarbonyloxyphenyl)acetamido]-2-oxo-1azetidinyl]-3-chloromethyl-3-butenoate diphenylmethyl 2-[4-chloro-3-[2-tetrahydropyranyloxy-2-(3-methoxymethoxyphenyl)acetamido]-2-oxo-1-azetidinyl]-3-chloromethyl-3-butenoate 4-methoxybenzyl 2-[4-chloro-3-[2-(t-butoxyformamido)-2-(4-chlorophenyl)acetamido]2-oxo-1-azetidinyl]-3-chloromethyl-3-butenoate phthalimidomethyl 2-[4-chloro-3-[2-benzyloxyformamido-2-(3-bromophenyl)acetamido]2-oxo-1-azetidinyl]-3-chloromethyl-3-butenoate benzyl 2-[4-chloro-3-[2-(2-methylphenyl)-2-(4-methoxybenzyloxyformamido)acetamido]-2-oxo-1-azetidinyl]-3-chloromethyl-3-butenoate 4-nitrobenzyl 2-[4-chloro-3-[2-(4-ethylphenyl)-2-(4-nitrobenzyloxyformamido)acetamido]2-oxo-1-azetidinyl]-3-chloromethyl-3-butenoate 4-methoxybenzyl 2-[4-chloro-3-[2-(3-propylphenyl)-2-(2,2,2-trichloroethoxyformamido)acetamido]-2-oxo-1-azetidinyl]-3-chloromethyl-3-butenoate t-butyl 2-[4-chloro-3-[2-(4-methoxyphenoxy)2,2-dimethylacetamido]-2-oxo-1-azetidinyl]-3-chloromethyl-3-butenoate triphenylmethyl 2-[4-chloro-3-[2-(3-isopropoxyphenoxy)-2,2-dimethylacetamido]-2-oxo1-azetidinyl]-3-chloromethyl-3-butenoate benzyl 2-[4-chloro-3-[2-(2-nitrophenoxy)-2,2-dimethylacetamido]-2-oxo-1-azetidinyl]-3-chloromethyl-3-butenoate methyl 2-[4-chloro-3-[2-(4-cyanophenoxy)-2,2-dimethylacetamido]-2-oxo-1-azetidinyl]-3-chloromethyl-3-butenoate ethyl (1α,5α)-2-(3-methoxy-2-thia-6-oxo-4,7-diazabicyclo[3.2.0]hept-3-en-7-yl)-3-chloromethyl-3-butenoate isopropyl (1α,5α)-2-(3-ethoxycarbonyl-2-thia-6-oxo-4,7-diazabicyclo[3.2.0]hept-3-en-7-yl)3-chloromethyl-3-butenoate 2,2,2-trichloroethyl (1α,5α)-2-(3-ethyl-2-thia-6-oxo-4,7-diazabicyclo[3.2.0]hept-3-en-7-yl)-3-chloromethyl-3-butenoate phthalimidomethyl (1α,5α)-2-[3-(2-butyl)-2-thia-6-oxo-4,7-diazabicyclo[3.2.0]hept-3-en-7yl]-3-chloromethyl-3-butenoate diphenylmethyl (1α,5α)-2-[3-(3-hexyl)-2-thia-6-oxo-4,7-diazabicyclo[3.2.0]hept-3-en-7yl]-3-chloromethyl-3-butenoate 4-nitroben±yl (1α,5α)-2-[3-(3-formyloxypentyl)-2-thia-6-oxo-4,7-diazabicyclo[3.2.0]hept-3-en-7-yl]-3-chloromethyl-3-butenoate 3-methoxybenzyl (1α,5α)-2-[3-(2-benzyloxyoctyl)-2-thia-6-oxo-4,7-diazabicyclo[3.2.0]hept-3-en-7-yl]-3-chloromethyl-3-butenoate benzyl (1α, 5α)-2-[3-(3-propoxypentyl)-2-thia-6-oxo-4,7-diazabicyclo[3.2.0]hept-3-en-7yl]-3-chloromethyl-3-butenoate 1,1-diethyl-2-butenyl (1α,5α)-2-[3-(1-cyanoethyl)-2-thia-6-oxo-4,7-diazabicyclo[3.2.0]hept-3en-7-yl]-3-chloromethyl-3-butenoate 1,1-dimethylallyl (1α,5α)-2-[3-(5-ethoxyheptyl)-2-thia-6-oxo-4,7-diazabicyclo[3.2.0]hept-3-en-7-yl]-3-chloromethyl-3-butenoate 1,1-dimethylpropyl (1α,5α)-2-[3-(3-cyanobutyl)-2-thia-6-oxo-4,7-diazabicyclo[3.2.0]hept-3-en-7-yl]-3-chloromethyl-3-butenoate butyl (1α,5α)-2-(3-vinyl-2-thia-6-oxo4,7-diazabicyclo[3.2.0]hept-3-en-7-yl)-3-chloromethyl-3-butenoate methyl (1α,5α)-2-[3-(3-pentenyl)-2-thia-6-oxo-4,7-diazabicyclo[3.2.0]hept-3-en-7-yl]-3-chloromethyl-3-butenoate diphenylmethyl (1α,5α)-2-[3-(3-triphenylmethoxy-2-butenyl)-2-thia-6-oxo-4,7-diazabicyclo[3.2.0]hept-3-en-7-yl]-3-chloromethyl-3-butenoate benzyl (1α,5α)-2-[3-(7-trimethylsilyloxy2,6-octadienyl)-2-thia-6-oxo-4,7-diazabicyclo[3.2.0-]hept-3-en-7-yl]-3-chloromethyl-3-butenoate 3-methoxybenzyl (1α,5α)-2-[3-(2-methoxyvinyl)-2-thia-6-oxo-4,7-diazabicyclo[3.2.0]hept-3-en-7-yl]-3-chloromethyl-3-butenoate 4-nitrobenzyl (1α,5)-2-[3-(3-ethoxy-3-butenyl)-2-thia-6-oxo-4,7-diazabicyclo[3.2.0]hept-3-en-7-yl]-3-chloromethyl-3-butenoate t-butyl (1α,5)-2-[3-(3-cyanoallyl)-2-thia-6-oxo-4,7-diazabicyclo[3.2.0]hept-3-en-7-yl]-3-chloromethyl-3-butenoate 4-methoxybenzyl (1α,5α)-2-[3-(6-cyano-2-octenyl)-2-thia-6-oxo-4,7-diazabicyclo[3.2.0]hept3-en-7-yl]-3-chloromethyl-3-butenoate 2,2,2-trichloroethyl (1α,5α)-2-[3-(3-cyclopropyl-2-thia-6-oxo-4,7-diazabicyclo[3.2.0]hept-3-3-en-7-yl)-3-chloromethyl-3-butenoate diphenylmethyl (1α,5α)-2-[3-(3-cyclohexyl-2-thia-6-oxo-4,7-diazabicyclo[3.2.0]hept-3-en-7-yl)3-chloromethyl-3-butenoate t-butyl (1α,5α)-2-[3-(3-phenoxycarbonyloxycyclobutyl)-2-thia-6-oxo-4,7-diazabicyclo[3.2.0-]hept3-en-7-yl]-3-chloromethyl-3-butenoate methyl (1α,5α)-2-[3-(3-benzyloxycyclopentyl)-2-thia-6-oxo-4,7-diazabicyclo[3.2.0]hept-3-en-7yl]-3-chloromethyl-3-butenoate diphenylmethyl (1α,5α)-2-[3-(4-methoxycyclooctyl)-2-thia-6-oxo-4,7-diazabicyclo[3.2.0]hept3-en-7-yl]-3-chloromethyl-3-butenoate methyl (1α,5α)-2-[3-(3-propoxycyclohexyl)2-thia-6-oxo-4,7-diazabicyclo[3.2.0]hept-3-en-7-yl]3-chloromethyl-3-butenoate 2,2,2-trichloroethyl (1α,5α)-2-[3-(2-ethoxycyclopropyl)-2-thia-6-oxo-4,7-diazabicyclo[3.2.0]hept3-en-7-yl]-3-chloromethyl-3-butenoate 4-nitrobenzyl (1α,5α)-2-[3-(3-cyanocyclobutyl)-2-thia-6-oxo-4,7-diazabicyclo[3.2.0]hept-3-en-7-yl]-3-chloromethyl-3-butenoate methyl (1α,5α)-2-[3-(5-cyanocyclooctyl)2-thia-6-oxo-4,7-diazabicyclo[3.2.0]hept-3-en-7-yl]3-chloromethyl-3-butenoate phthalimidomethyl (1α,-5α)-2-(3-phenoxymethyl-2-thia-6-oxo-4,7-diazabicyclo[3.2.0]hept3-en-7-yl)-3-chloromethyl-3-butenoate succinimidomethyl (1α,5α)-2-(3-benzyl2-thia-6-oxo-4,7-diazabicyclo[3.2.0]hept-3-en-7-yl)-3-chloromethyl-3-butenoate diphenylmethyl (1α,5α)-2-[3-[2-(3-chloroacetoxyphenyl)ethyl]-2-thia-6-oxo-4,7-diazabicyclo[3.2.0-]hept-3-en-7-yl]-3-chloromethyl-3-butenoate 3-methoxybenzyl (1α,5α)-2-[3-[2-(3-benzyloxyphenyl)ethoxymethyl]-2-thia-6-oxo-4,7-diazabicyclo[3.2.0]hept-3-en-7-yl]-3-chloromethyl-3-butenoate benzyl (1α,5α)-2-[3-[2-[2-(4-diphenylmethoxyphenyl)ethoxy]ethyl]-2-thia-6-oxo-4,7-diazabicyclo[3.2.0-]hept-3-en-7-yl]-3-chloromethyl-3-butenoate 3-nitrobenzyl (1α,5α)-2-[3-[α-trimethylsilyloxy-4-(4-nitrobenzyloxy)benzyl]-2-thia-6-oxo-4,7-diazabicyclo[3.2.0]hept-3-en-7-yl]-3-chloromethyl-3-butenoate methyl (1α,5α)-2-[3-(α-tetrahydropyranyloxy-4-methoxymethoxybenzyl)-2-thia-6-oxo-4,7-diazabicyclo[3.2.0]hept-3-en-7-yl]-3-chloromethyl-3-butenoate 3-nitrobenzyl (1α,5α)-2-[3-[α-(t-butoxyformamido)-3-chlorobenzyl]-2-thia-6-oxo-4,7-diazabicyclo[3.2.0]hept-3-en-7-yl]-3-chloromethyl-3-butenoate diphenylmethyl (1α,5α)-2-[3-(α-benzyloxyformamido)-3-bromobenzyl)-2-thia-6-oxo-4,7-diazabicyclo[3.2.0]hept-3-en-7-yl]-3-chloromethyl-3-butenoate methyl (1α,5α)-2-[3-[α-(4-nitrobenzyloxyformamido)-3-ethylbenzyl]-2-thia-6-oxo-4,7-diazabicyclo[3.2.0]hept-3-en-7-yl]-3-chloromethyl-3-butenoate diphenylmethyl (1α,5α)-2-[3-[α-(2,2,2-trichloroethoxyformamido)-4-propylbenzyl]-2-thia6-oxo-4,7-diazabicyclo[3.2.0]hept-3-en-7-yl]-3-chloromethyl-3-butenoate t-butyl (1α,5α)-2-[3-(α,α-dimethyl-4-methoxyphenoxymethyl)-2-thia-6-oxo-4,7-diazabicyclo[3.2.0]hept3-en-7-yl]-3-chloromethyl-3-butenoate 3-methoxybenzyl (1α,5α)-2-[3-(α,α-dimethyl2-isopropoxyphenoxymethyl)-2-thia-6-oxo-4,7-diazabicyclo[3.2.0]hept-3-en-7-yl]-3-chloromethyl-3-butenoate 2,2,2-trichloroethyl (1α,5α)-2-[3-(α,α-dimethyl-4-cyanophenoxymethyl)-2-thia-6-oxo-4,7diazabicyclo[3.2.0]hept-3-en-7-yl]-3-chloromethyl3-butenoate benzyl 2-(4-chloro-3-benzamido-2-oxo-1-azetidinyl)-3-chloromethyl-3-butenoate trimethylsilyl 2-[4-chloro-3-(3-methylbenzamido)-2-oxo-1-azetidinyl]-3-chloromethyl-3-butenoate diphenylmethyl 2-[4-chloro-3-(2-ethoxybenzamido)-2-oxo-1-azetidinyl]-3-chloromethyl-3-butenoate 4-nitrobenzyl (1α,5α)-2-(3-phenyl-2-thia6-oxo-4,7-diazabicyclo[3.2.0]hept-3-en-7-yl)-3-chloromethyl-3-butenoate benzyl (1α,α)-2-[3-(α-methylbenzyl)-2-thia-6-oxo-4,7-diazabicyclo[3.2.0]hept-3-en-7-yl]-3-chloromethyl-3-butenoate 4-methoxybenzyl (1α,5α)-2-[3-(4-chloro-α-butylbenzyl)-2-thia-6-oxo-4,7-diazabicyclo[3.2.0]-hept-3-en-7-yl]-3-chloromethyl-3-butenoate isopropyl 2-[4-chloro-3-[2-(4-cyanophenyl)-2-ethylacetamido]-2-oxo-1-azetidinyl]-3-chloromethyl-3-butenoate The preferred novel compounds of this invention are the compounds wherein R and $R^1$ are groups derived from the corresponding groups of readily available penicillins. Thus, the most highly preferred compounds of this invention are those wherein R is benzyl, phenyl, h-tolyl or phenoxymethyl, and $R^1$ is 4-nitrobenzyl, 4-methoxybenzyl, diphenylmethyl, benzyl or 2,2,2-trichloroethyl.

The azetidinones of this invention constitute one preferred class; the thiazolinoazetidinones constitute the most preferred class of compounds of this invention.

Thus, the following group of compounds represents most particularly preferred individual compounds of this invention.

4-nitrobenzyl 2-(4-chloro-3-phenylacetamido-2-oxo-1-azetidinyl)-3-chloromethyl-3-butenoate diphenylmethyl 2-(4-chloro-3-phenylacetamido-2-oxo-1-azetidinyl)-3-chloromethyl-3-butenoate 4-nitrobenzyl 2-[4-chloro-3-(4-methylbenzamido)-2-oxo-1-azetidinyl]-3-chloromethyl-3-butenoate diphenylmethyl 2-[4-chloro-3-(4-methylbenzamido)-2-oxo-1-azetidinyl]-3-chloromethyl-3-butenoate 4-nitrobenzyl 2-(4-chloro-3-phenoxyacetamido-2-oxo-1-azetidinyl]-3-chloromethyl-3-butenoate diphenylmethyl 2-(4-chloro-3-phenoxyacetamido-2-oxo-1-azetidinyl]-3-chloromethyl-3-butenoate 4-nitrobenzyl (1α,5α)-2-(3-benzyl-2-thia-6-oxo-4,7-diazabicyclo[3.2.0]hept-3-en-7-yl)3-chloromethyl-3-butenoate diphenylmethyl (1α,5α)-2-(3-benzyl-2-thia-6-oxo-4,7-diazabicyclo[3.2.0]hept-3-en-7-yl)3-chloromethyl-3-butenoate 4-nitrobenzyl (1α,5α)-2-[3-(4-methylphenyl)-2-thia-6-oxo-4,7-diazabicyclo[3.2.0]hept3-en-7-yl]-3-chloromethyl-3-butenoate diphenylmethyl (1α,5α)-2-[3-(4-methylphenyl)-2-thia-6-oxo-4,7-diazabicyclo[3.2.0]hept3-en-7-yl]-3-chloromethyl-3-butenoate 4-nitrobenzyl (1α,5α)-2-(3-phenoxymethyl-2-thia-6-oxo-4,7-diazabicyclo[3.2.0]hept3-en-7-yl)-3-chloromethyl-3-butenoate diphenylmethyl (1α,5α)-2-(3-phenoxymethyl-2-thia-6-oxo-4,7-diazabicyclo[3.2.0]hept3-en-7-yl)-3-chloromethyl-3-butenoate The process of this invention, by which are made the novel compounds of this invention, proceeds in a single step by contacting and reacting the starting compounds described above with either molecular chlorine or, preferably, t-butyl hypochlorite. A small amount of a $C_1$–$C_3$ carboxylic acid in the reaction mixture is needed.

The choice of solvent in which to run the reaction is not critical. The preferred solvents are the $C_2$–$C_8$ alkyl esters, such as ethyl acetate, ethyl formate, methyl acetate, butyl acetate, methyl formate, and the like. The esters are especially advantageous, because they ordinarily contain a small amount of free carboxylic acid which is sufficient to serve as the reaction initiator. However, many other solvents including ketones including acetone and methyl ethyl ketone, halogenated solvents such as dichloromethane, chloroform, 1,1-dichloroethane, chlorobenzene, bromobenzene and the like, acids including acetic acid and propionic acid, nitriles such as acetonitrile, and nitroalkanes such as nitromethane, are effectively used.

When the starting compound is a thiazolinoazetidinone, and molecular chlorine is used, it is necessary to include a hydrochloric acid scavenger in the reaction mixture, because free hydrochloric acid is likely to cause chlorination at the 3-position. Epoxides, especially propylene oxide and butylene oxide, are the preferred acid scavengers. Other basic compounds may also be used, however, especially basic salts such as the alkali metal salts of carboxylic acids, including sodium and potassium salts of formic and acetic acids. Still other bases, including inorganic bases such as the hydroxides, carbonates and bicarbonates of sodium, potassium and lithium, may also be used as acid scavengers.

The process of this invention proceeds in acceptable yields at convenient temperatures in the range of from about −20° C. to about 50° C.; the preferred temperature range is from about −10° C. to the ambient temperature.

The process of this invention gives excellent yields of the novel compounds of this invention. However, a certain amount of the corresponding 3-chloromethyl-2-butenoate is usually produced as a side product. This process usually gives about 4 parts of the desired novel compound and 1 part of the 2-butenoate.

The starting compounds used in the process of this invention are now known in the cephalosporin art. The thiazolinoazetidinones are most easily prepared as described by Cooper, U.S. Pat. No. 3,705,892, which illustrates the reaction of a penicillin sulfoxide with a trialkylphosphite or triphenylphosphine to prepare the desired starting thiazolinoazetidinone in a single step, in the 1α,5α epimeric form. The reaction is also discussed by Cooper and Spry in chapter 5 of *Cephalosporins and Penicillins*, Flynn, Editor, Academic Press, New York, 1972, at page 235.

The starting azetidinones are prepared as illustrated, for example, in U.S. Pat. No. 4,013,653, of Wolfe, and U.S. Pat. No. 3,860,577, of Kukolja. Kukolja shows that a penicillin can be reacted with a chlorinating agent to prepare an azetidinone in a single step. Kukolja's azetidinones have the side chain on the nitrogen atom in the form of a 2-butenoate rather than a 3-butenoate. The starting azetidinones used in the present process are obtained from the azetidinones of Kukolja as shown by Wolfe, supra, who brominates both of the terminal methyl groups of Kukolja's product, and then debrominates with zinc and an alkanoic acid to obtain the desired azetidinyl-3-butenoate which is a starting compound for the process of this invention.

The R groups of the starting compounds are derived from the corresponding 6-amido groups of the penicillin which is the ultimate starting compound. It will be recognized that the R groups are those which have been commonly seen on penicillin and cephalosporin antibiotics of the prior art. Antibiotic chemists will understand that the R groups of the starting compounds used in this invention are provided, in many cases, by deacylating the penicillin which is the ultimate starting compound, and reacylating with the desired group. Such steps are very old in the antibiotic art, of course, and have been well discussed by Kaiser and Kukolja in Chapter 3 of *Cephalosporins and Penicillins*, cited supra.

The following preparative examples are presented to assure that organic chemists can easily obtain any compound of this invention, and can carry out any process of this invention. The products of the examples were identified by various instrumental analytical techniques, as will be explained in the individual examples. When a given product was made repeatedly by different embodiments of the process of this invention, the product was often identified by thin-layer chromatography (TLC) or nuclear magnetic resonance analysis (NMR) as identical to the original sample, and was therefore not isolated or further analyzed.

EXAMPLE 1

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 5.83 g. portion of 4-nitrobenzyl (1α, 5α)-2-(3-phenoxymethyl-2-thia-6-oxo-4,7-diazabicyclo[3.2.0]-hept-3-en-7-yl)-3-methyl-3-butenoate was dissolved in 100 ml. of chloroform, and 4.1 g. of sodium acetate and 4.3 ml. of acetic acid were added. The mixture was stirred and cooled to −10° C. A 2.71 g. portion of t-butyl hypochlorite was dissolved in 5 ml. of chloroform and added to the reaction mixture over a period of 10 minutes. The reaction mixture was stirred at constant temperature for 2 hours, and was then poured into saturated aqueous sodium chloride solution. The organic layer was separated, extracted twice with portions of fresh brine and dried over magnesium sulfate. The dry organic layer was then evaporated under vacuum to obtain 6.5 g. of a light yellow oil which was purified by high pressure liquid chromatography, using a mixture of 15 parts of dichloromethane and 1 part of ethyl acetate as the eluting solvent. The product-containing fractions were combined and heated in methanol, whereupon crystallization began. A total of 2.34 g. of the desired product, m.p. 105.5°–107° C., was obtained.

Infrared analysis of the product, as a potassium bromide compact, showed maxima at 1795, 1787, 1770, 1755 and 1740 cm$^{-1}$. Ultraviolet analysis in methanol showed a lambda-maximum at 262 nm, ε 11,742.

Nuclear magnetic resonance analysis in CDCl$_3$ on a 360 megacycle instrument showed the following 67 values: 3.9 (q, J=12 Hz); 4.94 (q, J=14 Hz); 5.12(s); 5.23(s); 5.46(s); 5.88(d,J=4 Hz); 6.04 (d, J=4 Hz); 5.29 (q, J=14 Hz); 6.88-7.33(m); 7.48(d, J=8 Hz); 8.23(d, J=8 Hz)

EXAMPLE 2

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 4.67 g. portion of (1α,5α)-2-(3-phenoxymethyl-2-thia-6-oxo-4,7-diazabicyclo[3.2.0]hept-3-en-7-yl)-3-methyl-3-butenoate was dissolved in 250 ml. of ethyl acetate, and 10 ml. of propylene oxide was added. The mixture was stirred at room temperature while a solution of 0.35 g. of chlorine in carbon tetrachloride was added, and the mixture was stirred for 1 hour more. Successively, two additional 0.35 g. portions of chlorine were added, and the mixture was then cooled to 0° C. A fourth portion of chlorine was added, and the mixture was allowed to stand for 16 hours. The reaction mixture was then evaporated, and the resulting oil was purified by preparative thin-layer chromatography. The product-containing fractions were combined and evaporated to dryness to isolate the desired product as a pale yellow foam, which was identified as identical to the product of Example 1.

EXAMPLE 3

4-nitrobenzyl (1α,5α)-2-(3-phenoxymethyl2-thia-6-oxo-4,7-diazabicyclo[3.2.0]hept-3-en-7-yl)3-chloromethyl-3-butenoate A 920 mg. portion of 4-nitrobenzyl (1α,5α)-2-(3-phenoxymethyl-2-thia-6-oxo-4,7-diazabicyclo[3.2.0-]hept-3-en-7-yl)-3-methyl-3-butenoate was dissolved in 50 ml. of t-butyl acetate, and 0.07 g. of chlorine and 1 ml. of propylene oxide were added. The reaction was stirred at room temperature for 1 hour, and the reaction mixture was examined by nuclear magnetic resonance analysis. Signals indicating the presence of the desired product were observed.

EXAMPLE 4

4-nitrobenzyl (1α, 5α)-2-(3-phenoxymethyl2-thia-6-oxo-4,7-diazabicyclo[3.2.0]hept-3-en-7-yl)3-chloromethyl-3-butenoate The process of Example 3 was followed, except that methyl formate was used as the solvent. NMR analysis of the reaction mixture indicated the presence of the desired product, which was not isolated.

EXAMPLE 5

4-nitrobenzyl
(1α,5α)-2-(3-phenoxymethyl2-thia-6-oxo-4,7-diazabicyclo[3.2.0]hept-3-en-7-yl)3-chloromethyl-3-butenoate The process of Example 3 was repeated again, using dichloromethane as the solvent. Again, NMR analysis of the reaction mixture showed that the desired product was obtained, although it was not isolated.

EXAMPLE 6

4-nitrobenzyl
(1α,5α)-2-(3-phenoxymethyl-2-thia-6-oxo-4,7-diazabicyclo-[3.2.0]hept-3-en-7-yl)-3-chloromethyl-3-butenoate A 920 mg. portion of 4-nitrobenzyl (1α,5α)-2-(3-phenoxymethyl -2-thia-6-oxo-4,7-diazabicyclo-[3.2.0]hept-3-en-7-yl)-3-methyl-3-butenoate was dissolved in 50 ml. of methyl formate, and 1 ml. of propylene oxide and 0.2 g. of t-butyl hypochlorite were added. The reaction mixture was stirred for 1 hour at room temperature, at which time the reaction mixture was examined by NMR analysis, which showed the presence of a large amount of the desired product. The reaction mixture was evaporated under vacuum, and the residue was crystallized from methanol/diethyl ether to obtain 350 mg. of the desired product, identical to the product of Example 1.

EXAMPLE 7

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate The process of Example 3 was followed, except that sodium carbonate was used as the hydrochloric acid scavenger instead of propylene oxide. NMR analysis of the reaction mixture after 1 hour showed the presence of the desired product, which was not isolated.

EXAMPLE 8

4-nitrobenzyl
(1α,5α)-2-(3-benzyl-2-thia-6-oxo-4,7-diazabicyclo[3.2.0]hept-3-en-7-yl)-3-chloromethyl-3-butenoate A 450 mg. portion of 4-nitrobenzyl (1α,5α)-2-(3-benzyl-2-thia-6-oxo-4,7-diazabicyclo[3.2.0]hept-3-en-7-yl)-3-methyl-3-butenoate was dissolved in 50 ml. of methyl formate, and 0.5 ml. of propylene oxide was added. An 0.15 ml. portion of t-butyl hypochlorite was added, and the reaction mixture was stirred for 1 hour at room temperature. NMR analysis of the reaction mixture in CDCl$_3$ on a 60 megacycle instrument showed the presence of the desired product, which was not isolated. 3.6 (q, J=14 Hz); 3.84(s); 5.1(s); 5.25(s); 5.4(s); 5.86 (broad s); 7.28(s); 7.48 (d, J=8 Hz); 8.16 (d, J=8 Hz)

EXAMPLE 9

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate A 9.6 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 250 ml. of methyl formate and a 10 ml. portion of propylene oxide was added. The reaction mixture was stirred at 0° C., while a total of 4 ml. of t-butyl hypochlorite was added in 5 portions at intervals of approximately 5 minutes. Analysis of the reaction mixture by high pressure liquid chromatography showed that the amount of the desired product in the reaction mixture increased steadily with each addition of the hypochlorite, and that essentially complete conversion to the desired product occurred. The product was identified as identical to the product of Example 1.

EXAMPLE 10

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 25 ml. of methyl formate and 2 ml. of propylene oxide at room temperature. A 2.5 ml. portion of 1-molar chlorine solution in carbon tetrachloride was added dropwise over a 30 minute period. After the mixture had stood for 1.5 hours, an additional 2.5 ml. of the chlorine solution was added, and the reaction mixture was checked by thin-layer chromatography. An additional 1 ml. of chlorine solution was added, and the mixture was allowed to stand at room temperature for 16 hours. The mixture was then evaporated to dryness, and the residue was taken up in dichloromethane and precipitated by the addition of heptane. Analysis of the product by NMR showed that it was identical to the product of Example 1, although some impurities were present.

EXAMPLE 11

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 25 ml. of methyl formate, 170 mg. of sodium formate was added, and the mixture was cooled to −13° C. Six 0.1 ml. portions of t-butyl hypochlorite were added at intervals of about 5 minutes, while the temperature of the mixture rose to −3° C. NMR analysis of the reaction mixture showed that the reaction had gone essentially to completion and that the desired product was the major component of the reaction mixture.

EXAMPLE 12

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate The process of Example 11 was followed, except that 210 mg. of potassium formate was used as the base, and a few milligrams of 18-crown-6 was also added. The temperature of the reaction was from −1° C. to 8° C. Again, NMR analysis of the reaction mixture showed that the reaction had given an essentially complete yield of the desired product, identical to the product of Example 1.

EXAMPLE 13

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 25 ml. of methyl formate and cooled in an ice-methanol bath. A 680 mg. portion of sodium formate and 0.18 ml. of formic acid were added, and 0.6 ml. of t-butyl hypochlorite was added in 0.1 ml. portions while the temperature of the reaction mixture rose from −8° C. to −2° C. The mixture was stirred for a total of about 1.5 hours, while the temperature rose to 6° C. NMR analysis of the reaction mixture showed the presence of the desired product, identical to the product of Example 1.

EXAMPLE 14

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate The process of Example 13 was followed, except that the solvent was dichloromethane instead of methyl formate. The final reaction temperature was −1° C. in this instance. NMR analysis of the reaction mixture showed that somewhat less of the desired product was obtained and that the reaction mixture still contained some starting compound.

EXAMPLE 15

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-3.2.0]hept-3-en-7-yl)-3-methyl-3-butenoate was dissolved in 25 ml. of dichloromethane and cooled. An 0.38 ml. portion of formic acid and 0.81 ml. of pyridine were added to the reaction mixture, and 0.6 ml. of t-butyl hypochlorite was added portionwise while the temperature of the reaction mixture rose from −14° C. to −2° C. Analysis of the reaction mixture after about 1.5 hours showed that a moderate yield of the desired product, identical to the product of Example 1, was obtained.

EXAMPLE 16

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate The process of Example 13 was followed, except that the solvent was a mixture of 10 ml. of dichloromethane and 10 ml. of methyl acetate. The initial reaction temperature was −14° C., rising to −3° C. The mixture was stirred for about 1 hour, and was then evaporated under vacuum to dryness. The residue was purified over silica gel, using as solvent a mixture of 15 parts of dichloromethane and 1 part ethyl acetate. Analysis of the fractions removed from the column showed that the major product was the desired one, and that the corresponding 3-chloro-methyl-2-butenoate was a minor product.

EXAMPLE 17

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 10 ml. of methyl acetate and 10 ml. of dichloromethane, and the solution was cooled. An 0.5 ml. portion of acetic acid and 0.8 g. of sodium acetate were added to the reaction mixture, followed by 0.6 ml. of t-butyl hypochlorite in 0.1 ml. portions. The temperature of the mixture ranged from −5° C. to 3° C. during the addition. After 1 hour of stirring, the reaction mixture was evaporated to dryness under vacuum, and the residue was purified by chromatography over an 8-cm. column of silica gel, using the same eluting solvent as used in Example 16. The major product was the desired one, identical to the product of Example 1.

EXAMPLE 18

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate The process of Example 13 was carried out again, but without the formic acid, in order to ascertain the importance of the acid. Analysis of the reaction mixture by thin-layer chromatography at intervals showed that the reaction produced the desired product, but at a slower rate. Even after 5 days of standing at ambient temperature, the reaction was not complete.

EXAMPLE 19

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate An 0.26 ml. portion of 50 percent aqueous sodium hydroxide solution was added to 30 ml. of methyl formate with stirring. After about 20 minutes, 1.17 g. of 4-nitrobenzyl (1α,5α)-2-(3-phenoxymethyl-2-thia-6-oxo-4,7-diazabicyclo[3.2.0]hept-3-en-7-yl)-3-methyl-3-butenoate and 3 ml. of dichloromethane were added, and the reaction mixture was cooled. An 0.6 ml. portion of t-butyl hypochlorite was added in 0.1 ml. portions while the temperature rose from −5° C. to 0° C. After the mixture had stirred for 1 hour, it was analyzed by NMR and TLC, which analysis indicated that the desired product, identical to the product of Example 1, had been obtained.

EXAMPLE 20

4-nitrobenzyl
(1α,5α)-2-(3-phenoxymethyl-2-thia-6-oxo-4,7-diazabicyclo[3.2.0]hept-3-en-7-yl)-3-chloromethyl-3-butenoate The process of Example 17 was repeated, except that the solvent was 20 ml. of acetone, and the reaction temperature ranged from −10° C. to 1° C. Analysis by NMR and TLC showed that the desired product, identical to the product of Example 1, was obtained.

EXAMPLE 21

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate The process of Example 20 was repeated, except that the solvent was 25 ml. of 1,2-dichloroethane. Analysis of the reaction mixture by TLC and NMR methods showed that a yield of the desired product, identical to the product of Example 1, was obtained.

EXAMPLE 22

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo[3.2.0]hept-3-en-7-yl)-3-methyl-3-butenoate was dissolved in 20 ml. of 1,2-dichloroethane and the solution was cooled. A 1.14 ml. portion of acetic acid and 0.53 g. of sodium carbonate were added to the mixture, and 0.6 ml. of t-butyl hypochlorite was added in 0.1 ml. portions over a period of 1 hour while the temperature varied from −8° C. to 4° C. TLC analysis indicated that a good yield of the desired product, identical to the product of Example 1, was obtained.

EXAMPLE 23

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo[3.2.0]hept-3-en-7-yl)-3-methyl-3-butenoate was dissolved in 20 ml. of chloroform, and the solution was cooled. Then 0.34 g. of sodium formate and 0.19 ml. of formic acid were added, followed by six 0.1 ml. aliquots of t-butyl hypochlorite over a period of 70 minutes while the temperature rose from −10° C. to −1° C. TLC indicated that the reaction produced the desired compound, identical to the product of Example 1.

EXAMPLE 24

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo[3.2.0]hept-3-en-7-yl)-3-methyl-3-butenoate was dissolved in chloroform and the solution was cooled. An 0.82 g. portion of sodium acetate and 0.57 ml. of acetic acid were added, followed by 0.6 ml. of t-butyl hypochlorite in six 0.1 ml. portions over a period of 70 minutes while the temperature rose from −14° C. to −1° C. TLC analysis after 3 hours showed that the desired product, identical to the product of Example 1, was obtained.

EXAMPLE 25

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo[3.2.0]hept-3-en-7-yl)-3-methyl-3-butenoate was dissolved in chloroform and the mixture was cooled. Then 0.38 ml. of propionic acid and 0.48 g. of sodium propionate were added, and 0.6 ml. of t-butyl hypochlorite was added in the usual manner. The temperature varied from −15° C. to −3° C. over the 1-hour period of the additions. TLC analysis showed that the reaction produced a relatively small yield of the desired product after 75 minutes.

EXAMPLE 26

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate The process of Example 24 was repeated, except that the hypochlorite was added in one portion, when the temperature of the reaction mixture was −12° C. After 100 minutes, the temperature had risen to 9° C., and the course of the reaction was checked by TLC and NMR analysis, which indicated that the reaction was not complete but that the desired compound was obtained.

EXAMPLE 27

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo[3.2.0]hept-3-en-7-yl)-3-methyl-3-butenoate was dissolved in 20 ml. of chloroform and the solution was cooled. A 1.14 ml. portion of acetic acid and 0.82 g. of sodium acetate were added, and 3.5 ml. of 1-molar chlorine solution in carbon tetrachloride was added dropwise over a period of 5 minutes. The reaction temperature was −14° C. The mixture was stirred for 2 hours, and was then analyzed by TLC and NMR methods. An approximately 50 percent yield of the desired product, identical to the product of Example 1, was obtained.

EXAMPLE 28

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 4.68 g. portion of 4-nitrobenzyl (1α,5α)-2-(3-phenoxymethyl-2-thia-6-oxo-4,7-diazabicyclo[3.2.0]hept-3-en-7-yl)-3-methyl-3-butenoate was dissolved in 100 ml. of methyl formate and 5 ml. of butylene oxide was added, followed by 1.09 g. of t-butyl hypochlorite. The mixture was stirred at ambient temperature for 1 hour, after which an additional 0.3 ml. of the hypochlorite was added, and the mixture was stirred for 1 hour more. The reaction mixture was then poured into heptane, and was evaporated to an oil under vacuum. The residue was taken up in dichloromethane, filtered, and evaporated to dryness. The residue was then taken up in dichloromethane again, and purified by chromatography over silica gel. The product-containing fractions were analyzed by TLC and NMR methods, which indicated that the desired product, identical to the product of Example 1, was obtained.

EXAMPLE 29

4-nitrobenzyl (1α,5α)-2-(3-phenoxymethyl-2-thia-6-oxo-4,7-diazabicyclo[3.2.0]hept-3-en-7-yl)-3-thyl-3-butenoate An 0.46 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 25 ml. of acetonitrile at ambient temperature, and 0.12 ml. of t-butyl hypochlorite was added. The mixture was allowed to stand for 4 hours, after which analysis by TLC and NMR indicated that a yield of about 20 percent of the desired product, identical to the product in Example 1, had been obtained.

EXAMPLE 30

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate The process of Example 29 was repeated, using nitromethane as the solvent. After one-half hour of standing, the reaction produced about 25 percent of the desired product, as indicated by TLC and NMR analysis.

EXAMPLE 31

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 0.46 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 50 ml. of t-butyl acetate and 2 drops of formic acid was added. A 1 ml. portion of t-butyl hypochlorite was added in 1 portion and the mixture was stirred at room temperature for 16 hours. Analysis by TLC and NMR showed that a yield of the desired product was obtained.

EXAMPLE 32

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 35 ml. of methyl formate, and the reaction mixture was cooled to −10° C. Then 0.6 ml. of t-butyl hypochlorite was added in 0.05 ml. aliquots at intervals of 5 minutes, while the temperature rose to −3° C. Analysis by TLC and NMR showed that a good yield of the desired product was obtained.

EXAMPLE 33

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate The process of Example 32 was repeated, except that the solvent was ethyl formate. The result of this experiment was similiar to the result of the experiment of Example 32, in that a good yield of the desired product, identical to the product of Example 1, was obtained.

EXAMPLE 34

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo[3.2.0]-hept-3-en-7-yl)-3-methyl-3-butenoate was dissolved in 35 ml. of distilled methyl acetate. An 0.6 ml. portion of t-butyl hypochlorite was added in the same portionwise fashion used in Example 32, while the temperature varied from −20° C. to -6° C. Analysis by TLC and NMR showed that no reaction had occurred.

One drop of formic acid was added, followed by a further 0.6 ml. of the hypochlorite in 0.05 ml. aliquots at 5 minute intervals at temperatures from −5° C. to 2° C. Analysis by TLC and NMR showed this time that the desired product, identical to the product of Example 1, was obtained.

EXAMPLE 35

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 30 ml. of distilled methyl acetate and cooled. Then a few drops of trifluoroacetic acid were added, followed by 1.2 ml. of t-butyl hypochlorite over a period of 2 hours at temperatures from −5° C. to 1° C. Analysis by TLC and NMR showed approximately a 50 percent yield of the desired product, identical to the product of Example 1.

EXAMPLE 36

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 25 ml. of distilled methyl formate, and the solution was cooled. An 0.1 ml. portion of formic acid was added, followed by 0.6 ml. of t-butyl hypochlorite in 0.05 ml. aliquots over a period of 1 hour at temperatures from −13° C. to −3° C. Analysis by TLC and NMR showed that the desired product, identical to the product of Example 1, was obtained.

EXAMPLE 37

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 25 ml. of methyl formate, 0.1 ml. of dimethylformamide was added, and the solution was cooled. An 0.6 ml. portion of t-butyl hypochlorite was added in the same manner used in Example 36, while the temperature varied from −3° C. to 1° C. The desired product was obtained as indicated by TLC and NMR analysis.

EXAMPLE 38

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate The process of Example 37 was repeated, except that an 0.1 ml. portion of formic acid was added, and the temperature varied between −11° C. and 2° C. TLC and NMR analysis indicated that the desired product, identical to the product of Example 1, was obtained.

EXAMPLE 39

4-nitrobenzyl (1α,5α)-2-(3-phenoxymethyl-2-thia-6-oxo-4,7-diazabicyclo[3.2.0]hept-3-en-7-yl)-3-chloromethyl-3-butenoate A 1.17 g. portion of 4-nitrobenzyl (1α,5α)-2-(3-phenoxymethyl-2-thia-6-oxo-4,7-diazabicyclo-[3.2.0]hept-3-en-7-yl)-3-methyl-3-butenoate was dissolved in 25 ml. of methyl formate and 1 ml. of trimethyl orthoformate. The solution was cooled, and five 0.1 ml. aliquots of t-butyl hypochlorite were added over a period of 40 minutes at temperatures from −4° C. to 1° C. After 80 minutes, the mixture was analyzed by TLC and NMR methods, which showed that the desired product, identical to the product of Example 1, had been obtained.

EXAMPLE 40

4-nitrobenzyl (1α,5α)-2-(3-benzyl-2-thia-6-oxo-4,7-diazabicyclo[3.2.0]hept-3-en-7-yl)-3-chloromethyl-3-butenoate A 0.45 g. portion of 4-nitrobenzyl (1α,5α)-2-(3-benzyl-2-thia-6-oxo-4,7-diazabicyclo[3.2.0]-hept-3-en-7-yl)-3-methyl-3-butenoate was dissolved in 50 ml. of methyl formate, and 0.1 ml. of t-butyl hypochlorite was added. The mixture was allowed to stand at ambient temperature for 3 hours, and was then analyzed by NMR, which showed that the desired product, identical to the product of Example 8, had been obtained.

EXAMPLE 41 benzyl (1α,5α)-2-(3-phenoxymethyl-2-thia-6-oxo-4,7-diazabicyclo[3.2.0]hept-3-en-7-yl)-3-chloromethyl-3-butenoate A 0.42 g. portion of benzyl (1α,5α)-2-(3-phenoxymethyl-2-thia-6-oxo-4,7-diazabicyclo[3.2.0]-hept-3-en-7-yl)-3-methyl-3-butenoate was dissolved in 50 ml. of methyl formate, and 1 ml. of propylene oxide was added. The mixture was cooled to 0° C., and 0.15 ml. of t-butyl hypochlorite was added in 1 portion. The mixture stood for 30 minutes at 0° C., at which time analysis by nuclear magnetic resonance in CDCl$_3$ on a 60 megacycle instrument showed that the desired product had been obtained. 3.95(s); 4.85(s); 5.2 (broad s); 5.4(s); 5.8 (d, J=4 Hz); 5.92 (d, J=4 Hz); 6.8–7.5(m)

EXAMPLE 42 diphenylmethyl 2-(4-chloro-3-phenoxyacetamido-2-oxo-1-azetidinyl)-3-chloromethyl-3-butenoate A 5.18 g. portion of diphenylmethyl 2-(4-chloro-3-phenoxyacetamido-2-oxo-1-azetidinyl)-3-methyl-3-butenoate was dissolved in 200 ml. of methyl formate, and 1.71 ml. of t-butyl hypochlorite was added. The mixture was stirred at room temperature for 16 hours. It was then evaporated under vacuum to obtain a white foam, which was taken up in ethyl acetate and washed three times with water. The organic layer was then decolorized with activated carbon, dried over magnesium sulfate, and evaporated to a white foam. The foam was taken up in 100 ml. of dry diethyl ether, from which 1.12 g. of the desired product was obtained in crystalline form. The product was analyzed by infrared in chloroform, showing maxima at 1795, 1745 and 1695 cm$^{-1}$; a second spectrum in methanol showed maxima at 1775, 1740 and 1695 cm$^{-1}$. NMR analysis on a 100 megacycle instrument in CDCl$_3$ showed the following 6 values. 4.24(s); 4.63(s); 5.73(center of q); 6.2(d); 5.09(s); 5.33(s); 5.5(s)

EXAMPLE 43 diphenylmethyl 2-(4-chloro-3-phenoxyacetamido-2-oxo-1-azetidinyl)-3-chloromethyl-3-butenoate The process of Example 42 was repeated, on a scale twice as large, and quenching the reaction after two and one-half hours. Workup as performed in Example 42 provided 3.73 g. of the desired product, identical to the product of Example 42 by TLC and NMR analysis.

The novel compounds which have been described are used as intermediates in the preparation of cephalosporins and oxa-beta-lactams. The azetidinones of this invention are converted to the thiazolinoazetidinones of this invention by a step which was described by Kukolja and Lammert, U.S. Pat. No. 3,832,347. The azetidinone is first reacted with a halogenating agent such as phosphorus pentachloride to form the imino halide of the -NHCOR side chain. The imino halide is then reacted with hydrogen sulfide or a thioalkanoyl compound to prepare the thiazolinoazetidinone, having the unchanged 3-butenoate group, of this invention.

The thiazolinoazetidinones are used in various processes, one of which was described by Masi et al., U.S. Pat. No. 4,035,362. The compound is first treated with mild base, such as pyridine in an organic solvent, to convert the 3-butenoate group to a 2-butenoate group. The compound is then reacted with an azoderivative such as ethyl azodicarboxylate, which opens the thiazoline ring and forms an azetidinone having a 4-hydrazinothio group. That intermediate is reacted with a strong base in an anhydrous organic solvent to form a 3-chloromethyl-3-cephem, a useful intermediate for preparing cephalosporin antibiotics.

A preferred use of this invention is the preparation of 3-hydroxycephalosporins from the thiazolinoazetidinones of this invention. The reaction which prepares the 3-hydroxycephalosporins is readily performed as follows. The thiazolinoazetidinone is first reacted with ozone, in an inert solvent. The reaction is carried out at a temperature from about −100° C. to about 0° C., preferably at a temperature from about −80° C. to about −20° C. The ozonolysis may be done in any of many solvents including the halogenated hydrocarbons, such as chloroform, dichloromethane, 1,2-dichloroethane, bromoethane, carbon tetrachloride and the like. Ethers such as diethyl ether, tetrahydrofuran, diethylene glycol dimethyl ether, methyl ethyl ether and the like are likewise suitable. Further, alkanes such as hexane and octane, amides such as dimethylformamide and dimethylacetamide, alcohols including methanol and ethanol, and esters including ethyl acetate and methyl acetate, and mixtures of such solvents, may be used as solvents for the ozonolysis.

Reaction with ozone provides an ozonide involving the $C_3$–$C_4$ double bond of the 3-butenoate group. The ozonide is then reduced with a mild reducing agent to form the corresponding 4-chloro-3-oxobutyrate. The reduction is carried out with any of the agents commonly used for the decomposition of ozonides, including such agents as zinc or magnesium in the presence of water or acetic acid, alkali metal bisulfites, sulfur dioxide, trimethylphosphite, stannous chloride, Raney nickel, dialkyl sulfides and the like. Decomposition of the ozonide is accomplished by simply adding an excess of the reducing agent to the mixture containing the ozonide at a temperature from about $-80°$ C. to about $0°$ C.

Finally, the desired 3-hydroxycephalosporin is obtained by reacting the oxobutyrate obtained above with mild mineral acid. Acids such as hydrochloric acid, sulfuric acid, sulfonic acids such as methane-sulfonic acid and toluenesulfonic acid, and aqueous perchloric acid may be used, at temperatures from about $0°$ C. to about $50°$ C. The product has the R and $R^1$ groups of the thiazolinoazetidinone of this invention as its side chain and acid protecting group, respectively.

Thus, it will be understood that the range of 3-hydroxycephalosporins prepared by the exercise of this invention is defined by the range of thiazolinoazetidinones which has been discussed above. It is accordingly unnecessary to elaborate further on the 3-hydroxycephalosporin products.

3-Hydroxycephalosporins obtained by the above process have been well discussed in U.S. Pat. No. 3,917,587, of Chauvette, which thoroughly explains the use of such compounds as intermediates in preparing a number of useful antibiotics.

It will be understood that the cephalosporins which are prepared from the novel compounds of this invention have their carboxy groups, and any amino or hydroxy groups which may be on the amido side chains, in the blocked or protected form. Antibiotic chemists will of course understand that protecting groups must be removed before antibiotic use is made of such compounds.

The following preparative examples are shown to assure that the reader can use the thiazalinoazetidinones of this invention in the process of this invention for preparing 3-hydroxycephalosporins.

EXAMPLE A 4-nitrobenzyl 3-hydroxy-7-phenylacetamido-3-cephem-4-carboxylate

A portion of 4-nitrobenzyl (1α,5α)-2-(3-benzyl-2-thia-6-oxo-4,7-diazabicyclo[3.2.0]hept-3-en-7-yl)-3-chloromethyl-3-butenoate, prepared from 0.5 g. of the corresponding 3-methyl-3-butenoate, was dissolved in 20 ml. of dichloromethane and 10 ml. of methanol. The solution was cooled to $-78°$ C., and ozone was bubbled slowly through the solution until it turned blue. The temperature was held constant, and 0.5 g. of trimethylphosphite was added with stirring. The reaction mixture was then allowed to warm to ambient temperature, and was evaporated under vacuum to obtain a foam. Twenty ml. of methanol and 10 ml. of 1-normal hydrochloric acid were added to the foam, and the mixture was stirred for 5 minutes at $40°$ C. The mixture was then evaporated to dryness under vacuum, producing a foam which was analyzed by TLC and NMR, and found to consist in large part of the desired product. The following δ values were observed on the NMR spectrum. 2.53–1.70(q); 2.7(m); 4.4(q); 6.66(d); 5.03(d); 6.37(s); 6.68(2d)

Infrared analysis as a Nujol mull showed absorptions at 3.04, 5.60 and 6.0 microns.

EXAMPLE B 4-nitrobenzyl 3-hydroxy-7-phenoxyacetamido-3-cephem-4-carboxylate

A 480 mg. portion of 4-nitrobenzyl (1α,5α)-2-(3-phenoxymethyl-2-thia-6-oxo-4,7-diazabicyclo[3.2.0]hept-3-en-7-yl)-3-chloromethyl-3-butenoate was dissolved in 25 ml. of dichloromethane and 25 ml. of methanol and cooled to $-78°$ C. Ozone was bubbled through the solution with stirring until a blue color was observed, and then 1 g. of dimethyl sulfide was added. The reaction mixture was allowed to warm to ambient temperature, and was washed three times with saturated brine and dried over magnesium sulfate. Ten ml. of methanol and 5 ml. of 1-normal hydrochloric acid were added, and the mixture was stirred for 5 minutes at $40°$ C. It was then evaporated under vacuum to obtain a foam, which was analyzed and found to consist in large part of the desired compound.

I claim:
1. A compound of the formula

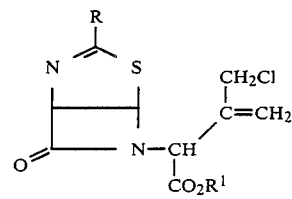

wherein
R is hydrogen,
methoxy,
$C_1$–$C_2$ alkoxycarbonyl,
$C_1$–$C_8$ alkyl,
$C_1$–$C_8$ alkyl monosubstituted with protected hydroxy, $C_1$–$C_3$ alkoxy or cyano,
$C_2$–$C_8$ alkenyl,
$C_2$–$C_8$ alkenyl monosubstituted with protected hydroxy, $C_1$–$C_3$ alkoxy or cyano,
$C_3$–$C_8$ cycloalkyl,
$C_3$–$C_8$ cycloalkyl substituted with protected hydroxy, $C_1$–$C_3$ alkoxy or cyano,

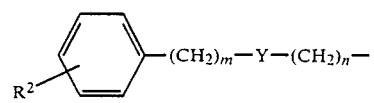

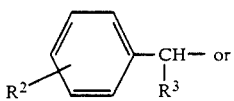

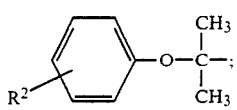

R² is hydrogen, protected hydroxy, chloro, bromo, C₁-C₃ alkyl, C₁-C₃ alkoxy, nitro or cyano;
Y is oxygen or a carbon-carbon bond;
R³ is protected hydroxy, C₁-C₄ alkyl or protected amino;
m is 0-2;
n is 0-2;
R¹ is a carboxylic acid protecting group; provided that the 1- and 5-position C-H bonds are in the α-position.

2. The compound of claim 1 which is 4-nitrobenzyl (1α,5α)-2-(3-phenoxymethyl-2-thia-6-oxo-4,7-diazabicyclo[3.2.0]hept-3-en-7-yl)-3-chloromethyl-3-butenoate.

3. The compound of claim 1 which is diphenylmethyl (1α,5α)-2-(3-phenoxymethyl-2-thia-6-oxo-4,7-diazabicyclo[3.2.0]hept-3-en-7-yl)-3-chloromethyl-3-butenoate.

4. A compound of claim 1 wherein R¹ is C₁-C₄ alkyl, C₄-C₆ t-alkyl, C₅-C₈ t-alkenyl, benzyl, methoxybenzyl, nitrobenzyl, diphenylmethyl, phthalimidomethyl, succinimidomethyl or trichloroethyl.

5. A compound of claim 4 wherein R is benzyl, phenyl, p-tolyl or phenoxymethyl.

6. A compound of claim 5 wherein R¹ is 4-nitrobenzyl, 4-methoxybenzyl, diphenylmethyl, benzyl or 2,2,2-trichloroethyl.

7. The compound of claim 1 which is 4-nitrobenzyl (1α,5α)-2-(3-benzyl-2-thia-6-oxo-4,7-diazabicyclo[3.2.0]hept-3-en-7-yl)-3-chloromethyl-3-butenoate.

8. The compound of claim 1 which is diphenylmethyl (1α,5α)-2-(3-benzyl-2-thia-6-oxo-4,7-diazabicyclo[3.2.0]hept-3-en-7-yl)-3-chloromethyl-3-butenoate.

9. The compound of claim 1 which is 4-nitrobenzyl (1α,5α)-2-[3-(4-methylphenyl)-2-thia-6-oxo-4,7-diazabicyclo[3.2.0]hept-3-en-7-yl]-3-chloromethyl-3-butenoate.

10. The compound of claim 1 which is diphenylmethyl (1α,5α)-2-[3-(4-methylphenyl)-2-thia-6-oxo-4,7-diazabicyclo[3.2.0]hept-3-en-7-yl]-3-chloromethyl-3-butenoate.

* * * * *